United States Patent [19]

Patell

[11] Patent Number: 4,900,559
[45] Date of Patent: Feb. 13, 1990

[54] STABILIZED ENTERIC COATED ASPIRIN GRANULES AND PROCESS OF PREPARATION

[75] Inventor: Mahesh K. Patell, Edison, N.J.

[73] Assignee: Briston-Myers Squibb Company, New York, N.Y.

[21] Appl. No.: 237,654

[22] Filed: Aug. 29, 1988

Related U.S. Application Data

[63] Continuation of Ser. No. 808,403, Dec. 12, 1985, abandoned.

[51] Int. Cl.$^4$ ................................................ A61K 9/26
[52] U.S. Cl. ................................... 424/470; 424/474; 424/475
[58] Field of Search ............... 424/459, 461, 462, 490, 424/468, 470; 514/165; 423/3

[56] References Cited

U.S. PATENT DOCUMENTS

| | | | |
|---|---|---|---|
| 2,990,328 | 6/1961 | Lincoln | 514/165 |
| 3,988,466 | 10/1976 | Takagi et al. | 514/423 |
| 4,017,647 | 4/1977 | Ohno et al. | 427/3 |
| 4,044,125 | 8/1977 | Walking | 514/234 |

Primary Examiner—Thurman K. Page
Assistant Examiner—Leon R. Horne
Attorney, Agent, or Firm—Morton S. Simon

[57] ABSTRACT

A stabilized enteric coated aspirin granule product prepared by commingling the enteric coated aspirin granules with glutamic acid hydrochloride.

11 Claims, No Drawings

STABILIZED ENTERIC COATED ASPIRIN GRANULES AND PROCESS OF PREPARATION

This application is a continuation of co-pending application Ser. No. 808,403, filed Dec. 12, 1985 and now abandoned.

This invention relates to enteric coated aspirin granules. More particularly it concerns enteric coated aspirin granules of improved stability.

Aspirin in granular form, and especially contained in capsules is currently a very popular dosage form for the administration of this drug. However, aspirin in this form as in other forms has presented problems with respect to gastric tolerance and as a consequence efforts have been made to overcome this by providing the granules with an enteric coating. As is well-known in this art enteric coated aspirin is generally not released in the stomach but rather is released when it passes into the intestine thus substantially avoiding the problem of gastric intolerance in the stomach.

In preparing enteric coated aspirin granules an unexpected problem was encountered. It was found that the stability of the aspirin granules when enteric coated was less than the uncoated granules. This was unanticipated since it was thought that the enteric coating of the aspirin granules might add a greater measure of stability to the granules.

It has now been discovered that the stability of enteric coated aspirin granules can be improved by the presence of glutamic acid hydrochloride. In the preferred form of this invention the enteric coated aspirin granules are dry blended with the glutamic acid hydrochloride; this product then being preferably filled into capsules such as gelatin capsules.

The U.S. Pat. No. 4044125 is concerned with the increase in the hydrolysis of aspirin in a product which is prepared by commingling d-propoxyphene hydrochloride with aspirin. The former, according to the patentee, is a pharmaceutically active ingredient used in the treatment of pain associated with trauma. When commingled with aspirin it increases both the amount and the rate of aspirin hydrolysis. He found that the hydrolysis of aspirin can be reduced in such a product by incorporating in it a hydrochloride of an amino acid such as glutamic acid hydrochloride. In accordance with this patent the combination of propoxyphene hydrochloride and the amino acid hydrochloride are granulated. These preformed granules are then commingled with aspirin. There is no teaching in this patent of the use of enteric coated aspirin granules as is characteristic of the present invention nor any suggestion of the problem that it is intended to solve.

The quantity of glutamic acid hydrochloride employed in the present invention is best related to the total weight of enteric coated aspirin granules that is utilized. This may vary over a range but ordinarily the quantity of the glutamic acid hydrochloride will amount to from about 1% to about 5% by weight based on the total weight of the enteric coated aspirin granules used with the preferred range being from about 2% to about 3% on the same weight bases.

The enteric coated aspirin granules contained in the compositions of this invention need not be of any special character. Any of a variety of enteric coated aspirin granules known to those skilled in this art may be used for the present purposes. The material used to form the enteric coating on the aspirin granules will ordinarily be a film forming polymer that is essentially insoluble in the gastric juices. These may be exemplified by such film forming polymers as polyvinyl acetate phthalate (PVAP), ethyl cellulose, cellulose acetate phthalate, hydroxypropyl methylcellulose phthalate, copolymers of methacrylic acid and acrylic acid esters. These polymers are well-known in the chemical arts and are available commercially. In this connection attention is invited to the following citations which are incorporated by way of reference;

(1) Polyvinyl Acetate Phthalate (PVAP); Colorcon, Inc. of West Point PA Technical Data Publication entitled "Polyvinyl Acetate Phthalate (PVAP); Enteric Polymer Tablet Sealant".

(2) Cellulose Acetate Phthalate; Eastman Products Publication No. 2FD-100C, entitled "Eastman C-A-P Cellulose Acetate Phthalate USP".

(3) Ethyl Cellulose; Hercules, Inc. Publication entitled "Ethyl Cellulose, Properties and Uses".

(4) Copolymers of methacrylic acid and acrylic acid esters; Rohm Pharma, Technical Applications Pamphlet (Infomation LD-11/E) entitled "EUDRAGIT L30D, Applications in the Production of Pharmaceutical Preparations".

(5) Hydroxypropyl methylcellulose phthalate; Shinestsu Chemical, of Japan, Technical Bulletin of HDMCP, Appendix II.

The amount of film forming enteric coating material that will be contained on the aspirin granules in accordance with the present invention will generally be within the range commonly found on such enteric coated aspirin granules that are known in this art. This will usually be in the range of from about 6% to about 12% by weight of enteric coating based on the total weight of the aspirin granules with the preferred range being from about 8% to about 10% on the same weight basis.

The enteric coated aspirin granules used for the present purpose will usually be prepared by coating aspirin granules with an enteric coating solution containing the polymeric film forming enteric coating material. The solvent for this solution may be any of a variety of solvents such as methylene chloride, methyl alcohol, isopropyl alcohol, acetone, triethyl acetate, ethyl alcohol, individually or in combination. However, the solvent of choice will usually be water.

In addition to the polymer film forming enteric coating material the enteric coating solution may also contain other adjuvants to facilitate the granulation process or to improve the character of the enteric coated granules. By way of illustration mention may be made of antiagglomerating agents (e.g. talcum powder); plasticizers (e.g. acetylated monoglycerides, diethyl phthalate, propylene glycol, polyethylene glycol); surfactants (e.g. Tweens & Spans); antifoaming agents (e.g. Medical Antifoam, AF Emulsion); anti-tack agents (mineral oil, stearic acid).

In preparing the enteric coated aspirin granules employed in the present invention the coating solution will generally first be prepared. This will usually comprise an aqueous medium in which the film forming enteric polymer and adjuvant, if any, will be dispersed. The quantity of enteric polymer that will be contained in this dispersion will usually be from about 5% to about 10% by weight based on the total weight of the composition. The enteric polymer aqueous dispersion is then sprayed onto the aspirin granules which are preferably preheated, and the coated granules are then dried. The weight ratio of coating dispersion to aspirin granules utilized in this process will generally be in the range of from about 12:88 to about 10:90.

In preparing the final products of this invention the enteric coated aspirin granules are mixed with glutamic acid hydrochloride this mixing preferably being accomplished by dry blending the enteric coated granules with the glutamic acid hydrochloride. In optional forms of this invention certain adjuvants may also be employed to aid in the blending operation or to improve the product characteristics. By way of example mention may be made of lubricants (e.g. zinc stearate), antiagglomerating agents (e.g. sodium lauryl sulfate).

It is generally anticipated that aspirin will be the essentially sole pharmaceutically active ingredient of the products of this invention. However, other pharmaceutically active ingredients may also be included without departing from its essential character.

In a preferred procedure a mix containing the glutamic acid hydrochloride and the adjuvants that may facilitate the preparation of the final products (e.g. lubricants, antiagglomerating agents) is first prepared and then properly sized by passing it through screens of appropriate mesh size. This, together with the aspirin granules prepared as described above will be dry mixed within an appropriate blender. For this purpose, for example a Twin Shell or Conical blender may be employed.

The particle sizes of the enteric coated aspirin granules and the glutamic acid hydrochloride that will comprise the products of this invention may vary somewhat. This to some extent will depend upon the dosage form that the product may take. In a preferred form of the present invention the enteric coated aspirin granules and the glutamic acid hydrochloride component will be contained in capsules and particularly gelatin capsules they may be swallowed conveniently. In this case the particle size of the enteric coated aspirin granules will be such as to pass through a screen of from about 16 mesh to about 40 mesh. The glutamic acid hydrochloride similarly will have a particle size such that it will pass through a screen of from about 30 mesh to about 40 mesh.

It is a feature of the present invention to provide a unit dosage form containing enteric coated aspirin granules commingled with a stabilizing amount of glutamic acid hydrochloride. A particularly useful unit dosage form is one in which these materials are contained in an edible capsule and preferably a gelatin capsule. The quantity of aspirin which will be contained in each capsule will vary with the dose of aspirin that is to be given and or the number of capsules which are to be administered. Generally, each capsule will contain from about 250 milligrams to about 650 milligrams of aspirin with the preferred range being from about 325 milligrams to about 500 milligrams per capsules.

The quantity of glutamic acid hydrochloride that will be used will be enough to stabilize the quantity of enteric coated aspirin granules contained in each capsule. This will usually be in the range of from about 5 milligrams to about 50 milligrams of glutamic acid hydrochloride per capsule with the preferred range being from about 10 milligrams to about 30 milligrams per capsule.

The enteric coating materials contained in each capsule is most conveniently expressed on a dry basis. This will usually amount to from about 5 milligrams to about 20 milligrams per capsule and preferably from about 7 milligrams to about 12 milligrams.

The following Examples are given to further illustrate this invention. It is to be understood, however, that the invention is not limited thereto.

EXAMPLE 1
RF. #2324

| DOSAGE UNIT AMT. MG/CAP. | ITEM NO. | INGREDIENTS | % EACH PART |
|---|---|---|---|
| | | Part I: Enteric Coated Aspirin Granules | |
| 326.633 | 1. | Aspirin as ASAGRAN 16/40 granules (Monsanto) weight taken based on 99.5% Assay Spec.) | 91.213 |
| 24.497* | 2. | Eudragit L-30D (30%/w applied as an aqueous dispersion) -(Rohm Pharm., GmbH Germany) | 6.841 |
| 4.354 | 3. | Talcum Powder, type 5251 (WCD) | 1.216 |
| 2.450 | 4. | Triethyl citrate F.C.C. (Citroflex-2) (Pfizer Inc.) | 0.684 |
| 0.165 | 5. | Medical antifoam emulsion (Dow Chem.) | 0.046 |
| —** | 6. | Water, deionized or distilled | — |
| (358.099) | | | 100.000 |
| | | Part II: Final blend for encapsulation | |
| 362.925 | 7 | Part I above (based on assay-90% aspirin) | 96.851 |
| 10.000 | 8. | Glutamic Acid HCl | 2.669 |
| 1.000 | 9. | Zinc Stearate (Mallinckrodt) | 0.267 |
| 0.800 | 10. | Sodium Lauryl Sulfate | 0.213 |
| 374.725 | | | 100.000 |

*Should be stored at temp. between 5-20° C.
**Evaporates during coating process. Code 0001 is an acceptable alternate.

Part I: Enteric Coated Aspirin Granules

Aspirin (item 1) is enteric coated using solution made from items 2, 3, 4, 5 & 6 using the following procedure:

Preparation of Coating Solution

1. Item 3 is suspended in water with high shear. Then add items 4 & 5; mix well.

2. Slowly add Item 2, mix very gently (higher shear causes coagulation of Item 2, which cannot be re-dispersed).

Coating Process

1. Item 1 is placed in fluid bed spray granulator/dryer (screen through #8 mesh if lumpy). (SWECO through 12/40 mesh screen, discard the fines, use granules left on 40 screen only.

2. Granules are preheated to about 50° C. exhaust temperature (approx. 2 min.).

3. Coating solution is sprayed at about 150 ml/min. with exhaust air temp. at 40°-45° C. with nozzle size 1.8 mm. After completion of the coating, the granules are dried for 20 min. with the inlet temp. reduced to 40° C.

Part II: Final blends for encapsulation

1. Mix items 8, 9, & 10 together, pass it thru a #30 screen.

2. Add item 7 to Twin Shell Blender; add above blend; mix well.

Capsule fill on Rotofill or H&K machine using pellet feeding device

Place above (Part II) granules in the hopper of the capsule filling machine and fill into capsules.

Eudragit L-30D is a copolymer, anionic in character, based on polymethacrylic acid and acrylic acid esters of formula:

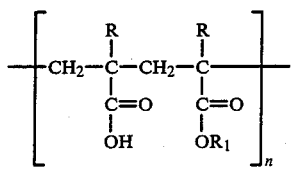

wherein n is a number; R is H or $CH_3$; and $R_1$ is $CH_3$ or $C_2H_5$

The ratio of the free carboxyl groups to the ester groups in this polymer is 1:1 and the mean molecular weight is 250,000.

Several enteric coated aspirin granules each with a different enteric coating materials were subjected to accelerated stability testing. Each formulation contained 325 mg aspirin enteric coated, 10 mg glutamic acid HCl and 1 mg zinc stearate. These were identified by the Codes CM 3124-3, CM 3124-4, CM 3124-5 and 3124-12.

A corresponding set of formulations with the same coatings but without glutamic acid was also prepared and identified by the Codes CM 3124-6, CM 3124-7, CM 3124-8 and 3124-13.

The compositions of each of the formulations are given below.

The identity of the enteric coating materials used to coat aspirin granules in Examples 2, 3, 4, 5, A, B, C and D is as follows:

1—BM Eudragit L30D: (See definition of EUDRAGIT L30D above)

2—Eurand America Inc.: Cellulose acetate phthalate; this is a polymer of glucose in which each glucose unit contains three hydroxyl groups. About half of hydroxyl groups are acetylated and about one-forth are esterified with one or two acid groups of phthalic acid.

3—Eli Lilly & Co.: Hydroxypropyl methyl cellulose phthalate, this is derived from hydroxypropyl methyl cellulose (NFXIII) by esterification with phthalic anhydride.

4—Reumyl: Cellulose Acetate phthalate—same as 2.

EXAMPLE 2
Enteric Coated Aspirin Capsules - CM 3124-3
Each Capsule contains:

| | |
|---|---|
| Enteric coated Aspirin (B-M Eudragit L30D) | 325 mg |
| Glutamic Acid Hydrochloride | 10 mg |
| Zinc Stearate | 1 mg |

EXAMPLE 3
Enteric Coated Aspirin Capsules - CM 3124-4
Each Capsule contains:

| | |
|---|---|
| Enteric coated Aspirin (Eurand America Inc.) | 325 mg |
| Glutamic Acid Hydrochloride | 10 mg |
| Zinc Stearate | 1 mg |

EXAMPLE 4
Enteric Coated Aspirin Capsules - CM 3124-5
Each Capsule contains:

| | |
|---|---|
| Enteric coated Aspirin (Eli Lilly & Co.) | 325 mg |
| Glutamic Acid Hydrochloride | 10 mg |
| Zinc Stearate | 1 mg |

EXAMPLE A
Enteric Coated Aspirin Capsules - CM 3124-6
Same as CM 3124-3, but without Glutamic Acid Hydrochloride.

EXAMPLE B
Enteric Coated Aspirin Capsules - CM 3124-7
Same as CM 3124-4, but without Glutamic Acid Hydrochloride.

EXAMPLE C
Enteric Coated Aspirin Capsules - CM 3124-8
Same as CM 3124-5, but without Glutamic Acid Hydrochloride.

EXAMPLE 5
Enteric Coated Aspirin Capsules - CM 3124-12
Each Capsule contains:

| | |
|---|---|
| Enteric coated Aspirin (from Reumuyl 500 mg) | 325 mg |
| Glutamic Acid Hydrochloride | 10 mg |
| Zinc Stearate | 1 mg |

EXAMPLE D
Enteric Coated Aspirin Capsules - CM 3124-13
Same as CM 3124-12, but without Glutamic Acid Hydrochloride.

The results of these tests are summarized in Table I below. the stability of the various formulations are measured by the quantity of salicylic acid generated per capsule from the hydrolysis of aspirin on storage at elevated temperature. The lower the analysis of salicylic acid per capsule the more stable the product.

TABLE I

| A. Formulations with Glutamic Acid | | | | |
|---|---|---|---|---|
| | mg/salicylic acid caps | | | |
| | Initial | 4 Days 60° C./60% RH* | 10 Days 50° C.** | 27 Days 50° C. |
| 3124-3 (Eudragit) | 0.6 | 4.1 | 1.6 | 2.5 |
| 3124-4 (Eurand) | 1.4 | 4.7 | 2.0 | 2.6 |
| 3124-5 (Lilly) | 1.7 | 5.2 | 2.3 | 3.3 |
| 3124-12 (Reumyl) | 1.9 | 6.0 | 2.9 | 4.0 |
| B. Formulations without Glutamic Acid | | | | |
| | Initial | 3 Days 60° C./60% RH | 10 Days 50° C. | 27 Days 50° C. |
| 33124-6 (Eudragit) | 0.6 | 33 | 6.1 | 19 |
| 3124-7 (Eurand) | 1.3 | 15 | 4.0 | 6.2 |
| 3124-8 (Lilly) | 1.8 | 14 | 4.1 | 6.8 |
| 3124-13 (Reumyl) | 1.9 | 12 | 4.4 | 6.3 |

*Average of two separate runs in the Analytical Department "torture chamber".
**Storage in HD/PE non-safety cap containers.

As can be seen from this data the formulations with glutamic acid were virtually indistinguishable chemically after 27 days at 50° C. and 4 days at 60° C./60% RH. The Eudragit formulation was slightly better than the others and the Reumyl was slightly worse; physically, all samples were acceptable after 27 days at 50° C.; the heat/humidity samples were all moderate to poor.

All formulations without glutamic acid demonstrated much worse chemical and physical stability than the corresponding glutamic acid formulations. However, the Eudragit samples were clearly much worse than the other three, and it can be seen that the Eudragit formulation was improved most by the addition of glutamic acid.

What is claimed is:

1. A unit dosage form consisting essentially of enteric coated aspirin granules commingled with an amount of glutamic acid hydrochloride powder sufficient to reduce hydrolysis of the aspirin in the enteric coated granules, wherein the glutamic acid hydrochloride is present in an amount of from about 1% to about 5% by weight, based on the total weight of the enteric coated aspirin granules, wherein the aspirin granules are enteric coated with an enteric material selected from the group consisting of polyvinyl acetate phthalate, ethyl cellulose, cellulose acetate phthalate, hydroxypropyl methylcellulose phthalate, copolymers of methacrylic acid and acrylic acid esters, and mixtures thereof.

2. The unit dosage form according to claim 1, wherein from about 2% to about 3% by weight, based on the total weight of the enteric coated aspirin granules, is present. group consisting of polyvinyl acetate phthalate, ethyl cellulose, cellulose acetate phthalate, hydroxypropyl methylcellulose phthalate, copolymers of methylacrylic acid and acrylic acid esters, and mixtures thereof.

3. The unit dosage form according to claim 1, wherein the enteric coated aspirin granules contain the enteric material in an amount of from about 6% to about 12% by weight, based on aspirin granule weight.

4. The unit dosage form according to claim 3, wherein the enteric material is present in an amount of from about 8% to about 10% by weight, based on aspirin granule weight.

5. The unit dosage form according to claim 1, wherein the glutamic acid hydrochloride has a particle size of from about 30 mesh to about 40 mesh and the enteric coated aspirin granules have a particle size of from about 16 mesh to about 40 mesh.

6. The unit dosage form according to claim 1, where the enteric coated aspirin granules and the glutamic acid hydrochloride are commingled by dry blending.

7. The unit dosage form according to claim 1, wherein the unit dosage form is a gelatin capsule containing a dry blend of the enteric coated aspirin granules and the glutamic acid hydrochloride powder.

8. The unit dosage form according to claim 7, wherein from about 250 mg to about 650 mg of aspirin and from about 5 mg to about 50 mg of glutamic acid hydrochloride are present.

9. The unit dosage form according to claim 7, wherein from about 325 mg to about 500 mg of aspirin and from about 10 mg to about 30 mg of glutamic acid hydrochloride are present.

10. The unit dosage form according to claim 7, wherein the capsule contains, on a dry basis, from about 5 mg to about 20 mg of enteric coating material.

11. The unit dosage form according to claim 7, wherein the capsule contains, on a dry basis, from about 7 mg to about 12 mg of enteric coating material.

* * * * *

UNITED STATES PATENT AND TRADEMARK OFFICE
CERTIFICATE OF CORRECTION

PATENT NO. : 4,900,559
DATED : Feb. 13, 1990
INVENTOR(S) : Mahesh K. Patell

It is certified that error appears in the above-identified patent and that said Letters Patent is hereby corrected as shown below:

Cover page item [73] Assignee: change "Briston" to --Bristol--

Signed and Sealed this

Twenty-second Day of January, 1991

Attest:

HARRY F. MANBECK, JR.

*Attesting Officer*  *Commissioner of Patents and Trademarks*